United States Patent [19]
Bormann et al.

[11] Patent Number: 5,738,796
[45] Date of Patent: Apr. 14, 1998

[54] METHOD FOR SEPARATING COMPONENTS FROM A BIOLOGICAL FLUID

[75] Inventors: Thomas J. Bormann, Melville; Frank R. Pascale; Thomas C. Gsell, both of Glen Cove, all of N.Y.

[73] Assignee: PALL Corporation, East Hills, N.Y.

[21] Appl. No.: 676,093

[22] Filed: Jul. 2, 1996

Related U.S. Application Data

[63] Continuation of Ser. No. 202,111, Feb. 25, 1994, Pat. No. 5,545,339.

[51] Int. Cl.$^6$ .......................... B01D 37/00; B01D 21/26; B01D 36/00; A61M 1/00
[52] U.S. Cl. .......................... 210/806; 210/767; 210/782; 210/787; 210/789; 210/805; 494/36; 494/37; 604/4; 604/5; 604/6
[58] Field of Search .................. 210/767, 782, 210/787, 789, 805, 806; 95/241, 273; 494/36, 37; 604/4, 5, 6

[56] References Cited

U.S. PATENT DOCUMENTS

| | | |
|---|---|---|
| 3,802,432 | 4/1974 | Djerassi . |
| 3,892,236 | 7/1975 | Djerassi . |
| 4,197,847 | 4/1980 | Djerassi . |
| 4,362,155 | 12/1982 | Skurkovich . |
| 4,512,763 | 4/1985 | Schneider ........................ 604/5 |
| 4,613,322 | 9/1986 | Edelson .......................... 604/6 |
| 4,680,025 | 7/1987 | Kruger et al. ..................... 604/6 |
| 4,776,964 | 10/1988 | Schoendorfer et al. ............ 210/782 |
| 4,880,548 | 11/1989 | Pall et al. ..................... 210/767 |
| 4,898,573 | 2/1990 | Takenaka et al. ................ 604/6 |
| 4,923,620 | 5/1990 | Pall .......................... 210/767 |
| 4,925,572 | 5/1990 | Pall .......................... 210/767 |
| 4,935,002 | 6/1990 | Gordon ......................... 604/4 |
| 5,100,564 | 3/1992 | Pall et al. ..................... 210/782 |
| 5,104,373 | 4/1992 | Davidner et al. ................ 604/4 |
| 5,112,298 | 5/1992 | Prince et al. ................... 604/6 |
| 5,123,901 | 6/1992 | Carew ......................... 604/5 |
| 5,126,054 | 6/1992 | Matkovich ..................... 210/641 |
| 5,217,627 | 6/1993 | Pall et al. ..................... 210/782 |
| 5,229,012 | 7/1993 | Pall et al. ..................... 210/767 |
| 5,269,946 | 12/1993 | Goldhaber et al. .............. 210/767 |
| 5,281,342 | 1/1994 | Biesel et al. .................. 210/782 |
| 5,298,016 | 3/1994 | Gordon ........................ 609/4 |
| 5,302,299 | 4/1994 | Pascale et al. ................. 210/767 |
| 5,427,695 | 6/1995 | Brown ......................... 210/782 |
| 5,451,321 | 9/1995 | Matkovich ..................... 210/641 |
| 5,472,621 | 12/1995 | Matkovich et al. .............. 210/767 |

FOREIGN PATENT DOCUMENTS

| | | |
|---|---|---|
| 8605999 | 10/1986 | WIPO . |
| 9000069 | 1/1990 | WIPO . |
| 9104088 | 4/1991 | WIPO . |
| 9207656 | 5/1992 | WIPO . |
| 9308904 | 5/1993 | WIPO . |
| 9324157 | 9/1993 | WIPO . |
| 9324157 | 12/1993 | WIPO . |
| 9401193 | 1/1994 | WIPO . |

*Primary Examiner*—John Kim
*Attorney, Agent, or Firm*—Leydig, Voit & Mayer, Ltd.

[57] ABSTRACT

The present invention provides for processing a biological fluid such as blood, to separate at least one component from the biological fluid, and to remove leukocytes from the separated component while returning the component depleted biological fluid to the source of the fluid. Illustratively, blood is obtained from a source such as a donor, and platelets are separated from the bold. Gas is separated from the flow path of the separated platelets, which are depleted of leukocytes, while platelet depleted blood is returned to the donor.

24 Claims, 2 Drawing Sheets

METHOD FOR SEPARATING COMPONENTS FROM A BIOLOGICAL FLUID

This application is a continuation of patent application Ser. No. 08/202,111, filed Feb. 25, 1994, now U.S. Pat. No. 5,545,339.

TECHNICAL FIELD

This invention relates to methods, systems, and devices for processing a biological fluid, preferably including processing a separated component of the biological fluid. More particularly, the present invention concerns obtaining blood from a source such as a donor, separating a component from the blood, treating the separated component, and returning the component depleted blood to the source.

BACKGROUND OF THE INVENTION

An adult human contains about 5 liters of blood, which includes valuable components such as red blood cells, liquid blood plasma and platelets. In view of the substantial therapeutic and monetary value of these blood components, a variety of techniques have been developed to separate blood into its component fractions while ensuring maximum purity and recovery of each of the components. Additionally, since blood and blood components may include varying numbers of white blood cells (leukocytes), which may cause undesirable effects when administered to a patient, blood processing techniques may also include leukocyte depleting the blood or blood components, e.g., by passing the blood or blood components through a leukocyte depletion device.

In some techniques for blood processing, a container such as a flexible bag is connected to a blood donor, and filled with a unit of whole blood. The container is disconnected from the donor, and the blood is further processed to provide the desired separated component(s). Alternatively, in some other techniques, e.g., apheresis, the donor may remain connected to a blood processing system during component separation, while the remainder of the blood, depleted of the desired component, is returned to the donor. Blood may be passed transversely across a membrane, e.g., a planar sheet or a bundle of hollow fibers, to separate the component from the blood. Typically, centrifugation is employed to separate the component from the blood. The separated component may be returned to the donor, or collected for a later use, such as a transfusion.

There are a variety of apheresis procedures, which may be generally classified according to the particular component to be separated and/or the method of separation. For example, the separation of platelets during apheresis is known as plateletpheresis or thrombocytapheresis, the separation of young red blood cells is known as neocytapheresis, and the separation of plasma is known as plasmapheresis.

With respect to classification by the mode of separation, among those procedures are methods including continuous flow, and intermittent flow. Typically, during continuous flow, blood is withdrawn from a donor from one venipuncture site using a pump, processed to separate at least one desired component, and the component depleted blood is returned to the donor through a second venipuncture site, essentially simultaneously, using an additional pump.

Typically, during intermittent flow, which utilizes a single venipuncture site, blood is withdrawn from an individual using a pump, and the blood is processed to separate at least one component. The pump is then reversed to return the component depleted blood to the donor. These cycles of withdrawal and return may be repeated as necessary until the desired amount of separated component is obtained. For example, during intermittent flow plateletpheresis, there may be several cycles of withdrawal of blood from the donor and separation of platelet-containing fluid from the blood, followed by return of the platelet-depleted red cell-containing blood, to the donor, to obtain a therapeutic dose of platelets.

Continuous flow and intermittent flow apheresis protocols may include centrifugation, and those techniques including centrifugation are typically referred to as continuous flow centrifugation (CFC), and intermittent flow centrifugation (IFC), respectively. Typically, during these protocols, blood may be spun in a centrifuge bowl and/or exposed to a rotating membrane to separate the desired component(s).

There are a number of drawbacks associated with apheresis systems, particularly with respect to processing the separated component. For example, during continuous flow and intermittent flow plateletpheresis, since a limited volume of blood may be withdrawn from the donor at any given time, some methods include accumulating or pooling the separated platelets until almost the entire procedure, i.e., the separation of the desired amount of platelets, is complete. The apheresis system is then disconnected from the donor, and the accumulated platelets may be leukocyte depleted, e.g., by passage through a leukocyte depletion device. This is a time consuming, inefficient process, in that extra time is required to leukocyte deplete the large quantity of accumulated platelets after plateletpheresis is completed. Similar drawbacks are associated with other apheresis protocols, e.g., involving accumulating and leukocyte depleting other components, such as red cells and/or plasma.

Among other disadvantages, the leukocyte depletion of the accumulated component, e.g., platelets, requires the use of a correspondingly larger leukocyte depletion device to obtain a desired leukocyte depletion efficiency in an acceptable amount of time. Furthermore, due to its larger size, the device may hold up an increased amount of valuable platelets which may be difficult to recover in a cost effective manner.

Additionally, the presence of air or gas, for example, in a container with the separated component, in the fluid flow path of the separated component and/or in the component fluid itself, may adversely affect processing efficiency and/or impair the quality of the component and may decrease its storage life. For example, since the platelet containing fluid may displace gas as it passes from one location to another, it may be difficult and/or time consuming to efficiently pass the fluid through a porous medium such as a leukocyte depletion medium, since the displaced gas may block the medium. Similarly, since the platelet containing fluid may be "foamy," i.e., include air bubbles, the presence of air may present difficulties when the fluid is to be passed through a porous medium such as a leukocyte depletion medium. Moreover, oxygen may be associated with an increased metabolic rate (during glycolysis), which may lead to decreased storage life and decreased viability and function of blood components such as red cells and/or platelets. Thus, it may be desirable to minimize the presence of air when blood components are being processed and/or before the blood components are stored, particularly when they are to be stored for long periods of time, e.g., several days or more.

Accordingly, there is an unaddressed need in the art for providing leukocyte depletion during apheresis, thereby decreasing the time needed to separate and leukocyte deplete a blood component. There is also a need for a system that provides for minimizing the presence of air while processing the separated component, e.g., while passing the separated component through a porous medium, and/or for minimizing the presence of air before storing the separated component.

Moreover, there is a particular need for a system that is compatible with existing systems, including automated systems, and provides for separation of a component of blood, separation of air from the component flow path, and leukocyte depletion of the component, preferably without extending the time that the donor is attached to the processing system.

These and other advantages of the present invention will be apparent from the description as set forth below.

SUMMARY OF THE INVENTION

Processes, systems and devices according to the instant invention provide for withdrawal of a biological fluid from a source, separation of a component of the biological fluid, return of the component depleted biological fluid to the source, and leukocyte depletion of a portion of the separated component before the return of the component depleted biological fluid to the source is completed. Preferably, when the source of the biological fluid is a donor, the instant invention provides for separation and leukocyte depletion of a component of a biological fluid substantially contemporaneously with the return of the biological fluid to the donor.

The instant invention also provides for separation of a component of a biological fluid and separation of gas from the flow path of a portion of the separated component, before the return of the component depleted biological fluid to the source is completed. Preferably, when the separated component flow path includes a porous medium, e.g., a filter assembly including an inlet and an outlet, and a porous medium interposed across the flow path between the inlet and the outlet, the instant invention provides for separation of gas from the fluid flow path of the separated component upstream of the porous medium, i.e., so that gas neither contacts nor passes through the porous medium.

The instant invention may be used in a semi-automated or automated system, and provides for the separation of gas from the flow path of the separated component, and for efficient leukocyte depletion of the separated component.

In accordance with the invention, the separated component may be leukocyte depleted while the remaining component depleted biological fluid is being returned to the donor. This eliminates or decreases the time required for post apheresis leukocyte depletion, since the separated component, e.g., platelets, may be leukocyte depleted while the remaining biological fluid, for example, red cell containing platelet-depleted fluid, may be returned to the donor.

Since the separated component need not be accumulated before leukocyte depletion, the leukocyte depletion device can be smaller, resulting in a cost savings since less valuable fluid is "lost" due to fluid hold up of the smaller device. Moreover, there may be an additional cost savings resulting from the use of smaller devices.

Additionally, leukocyte depletion efficiency can be increased by, for example, controlling the flow rate of fluid through the leukocyte depletion device, without additionally inconveniencing the donor, since leukocyte depletion of the separated component can be performed substantially contemporaneously with the return of the component depleted fluid toward the donor. Thus, for example, a decreased flow rate of the separated component through the leukocyte depletion device need not extend the time that the donor remains attached to the system, since the flow rate of the component depleted fluid back to the donor may remain unchanged.

The instant invention is particularly useful when there are a plurality of donors to be sequentially connected to the apheresis system, e.g., at a donation center, since it minimizes the time that the machine will be unavailable between donations. Since biological fluid must be cleared from the apheresis system before it can be connected to the next donor, the present invention, in which leukocyte depletion of the separated component may be essentially completed as the system is disconnected from the donor, minimizes the amount of fluid to be cleared from the apheresis system between donations. As a result, less time is required to clear the system before the next donation.

SPECIFIC DESCRIPTION OF THE INVENTION

A method in accordance with the invention comprises processing a biological fluid through one or more cycles of: obtaining biological fluid from a source, separating at least one component from the biological fluid, and returning the component depleted biological fluid to the source; and, while processing the biological fluid, at least one of (1) separating gas from the flow path of the separated component by passing a portion of the separated component through a gas separation arrangement and (2) passing a portion of the separated component through a leukocyte depletion medium.

A method in accordance with the invention includes obtaining a biological fluid from a source, separating at least one component from the biological fluid, passing the component depleted biological fluid toward the source of the biological fluid while leukocyte depleting a portion of the separated component by passing the separated component through a leukocyte depletion medium.

The present invention also provides a method for processing a biological fluid including obtaining a biological fluid from a source, separating at least one component from the biological fluid, passing the component depleted biological fluid toward the source of the biological fluid while passing a portion of the separated component into a gas separation arrangement to separate gas from the flow path of the separated component.

In a more preferred embodiment, a method in accordance with the present invention includes separating gas from the flow path of the separated component and depleting leukocytes from a portion of the separated component, while returning the component depleted biological fluid to the source.

The present invention also provides a system comprising a conduit having a first end suitable for providing fluid communication with a component separation device, and a second end suitable for providing fluid communication with a receiving container; and, interposed between the second end of the conduit and the receiving container, at least one of a gas separation arrangement and a leukocyte depletion device.

In accordance with the invention, a system is provides comprising a first container for holding a separated leukocyte containing component of a biological fluid; a second container for holding a separated leukocyte depleted component of a biological fluid; a gas separation arrangement including a porous medium; and, a filter assembly comprising a leukocyte depletion medium; said gas separation arrangement and said filter assembly interposed between the first container and the second container.

In accordance with the invention, biological fluid includes any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelets suspended in plasma, platelet concentrate (PC), platelet-rich plasma (PRP), platelet-free plasma, platelet-poor plasma (PPP), plasma, packed red cells (PRC), transition zone material, buffy coat; analogous blood products derived from blood or a blood component of derived from bone marrow; red cells suspended in physiological fluid; and platelets suspended in physiological fluid. The biological fluid may include leukocytes, or may be treated to remove leukocytes. As used herein, biological fluid refers to the components described above, and to similar blood products obtained by other means and with similar properties.

A biological fluid processing system according to the invention is compatible with a wide variety of component separation systems and/or component separation devices. Thus, a biological fluid processing system as disclosed herein may be placed in fluid communication with, for example, an apheresis system including a separation device for separating at least one component from a biological fluid.

Typically, the biological fluid processing system includes at least one of a gas separation arrangement and a filter assembly comprising a leukocyte depletion device, in fluid communication, via at least one conduit, with at least one container. Generally, the system includes two or more conduits, and at least one conduit is suitable for providing fluid communication with the component separation device. More preferably, a biological fluid processing system for connection to a separation device in accordance with the invention includes at least two containers, with a gas separation arrangement and a filter assembly interposed between the containers.

Figure 1:
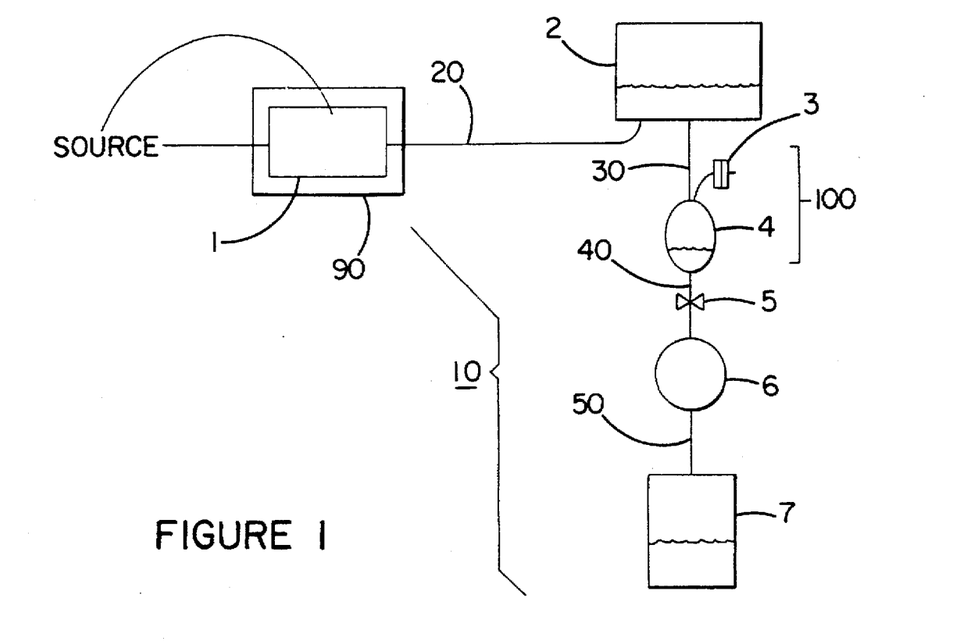
FIG. 1 is an embodiment of the present invention including a gas separation arrangement and a filter assembly.

In the embodiment illustrated in FIG. 1, which includes an apheresis separation system 90 including a component separation device 1, the separation device is in fluid communication with a biological fluid processing system 10. The illustrated biological fluid processing system 10 includes a conduit 20 having a first end and a second end, wherein the ends are suitable for fluid communication with both the separation system, and another element of the biological fluid processing system. In another embodiment, the apheresis separation system 90 includes a conduit for providing fluid communication with both the apheresis system 90 and an element of the biological fluid processing system 10.

In the embodiment illustrated in FIG. 1, one end of conduit 20 is in fluid communication with at least one container 2, such as a holding container. Downstream of the holding container 2 is a filter assembly 6 and another container 7, such as a receiving or collection container. In this illustrated embodiment, which includes conduits 30, 40, and 50, and provides for separation of gas from the flow path of the separated component of the biological fluid, the biological fluid processing system 10 includes a gas separation arrangement 100 comprising a gas collection device 4 such as a drip chamber and a gas separation device 3 such as a vent, which are interposed between the holding container 2 and the filter assembly 6.

The system may include at least one flow control device such as a clamp associated with at least one conduit and/or container. In the illustrated embodiments, the biological fluid processing system includes flow control device 5. Preferably, as shown in the illustrated embodiments, the flow control device 5 is interposed between the gas separation arrangement 100 and the filter assembly 6. In the embodiment illustrated in FIG. 4, the system includes additional flow control devices 210, 220, 230 and 240.

The biological fluid processing system may include a gas collection and displacement loop which preferably includes at least one conduit, and at least one of a gas collection and displacement container and a liquid barrier medium. In another embodiment, the system may include a sampling arrangement, which preferably includes at least one conduit and a satellite container such as a sampling container.

Figure 4:
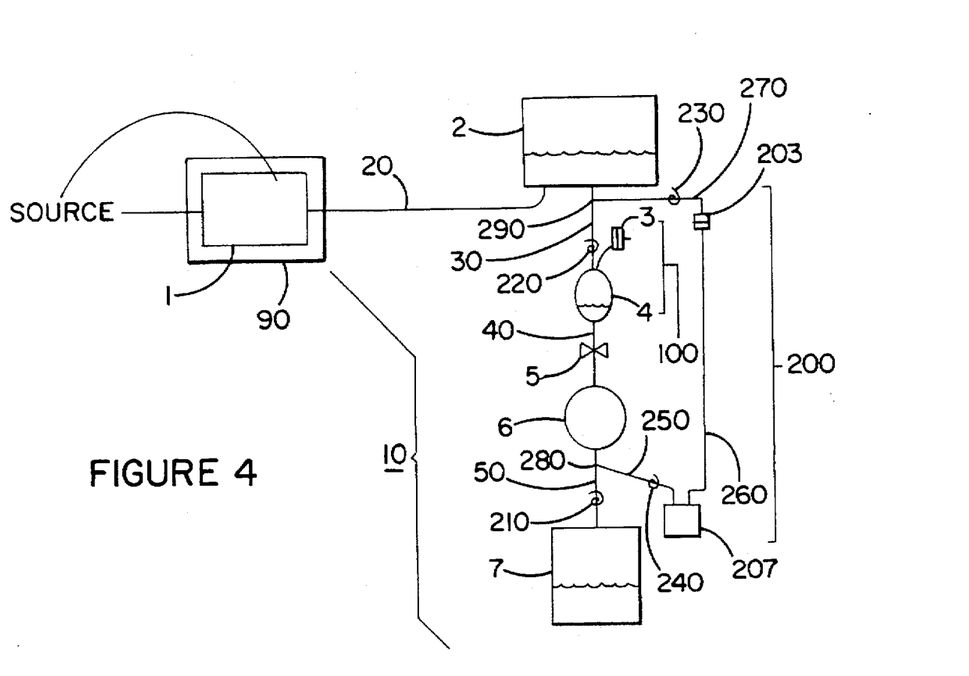
FIG. 4 is an embodiment of the present invention including a gas separation arrangement and a filter assembly, as well as a gas collection and displacement loop.

In the embodiment illustrated in FIG. 4, the system includes a gas collection and displacement loop 200, which includes a gas collection and displacement container 207, a liquid barrier assembly 203, and conduits 250, 260, and 270. Preferably, at least one flow control device such as a clamp may be associated with the gas collection and displacement loop 200. In the illustrated embodiment, flow control devices 230 and 240 associated with conduits 270 and 250, respectively, of the gas collection and displacement loop 200.

Each of the components or element is of the invention will now be described in more detail below.

As illustrated in the Figures, e.g., FIG. 1, an apheresis separation system 90 including a separation device 1 may be used to separate at least one component from a biological fluid.

A variety of devices and/or systems for separating at least one component from a biological fluid are suitable for carrying out the invention. These devices and/or systems may provide for separation without centrifugation, e.g., by exposing the biological fluid to a porous separation medium such as a planar sheet or a bundle of hollow fibers, and/or they may provide for separation by centrifugation, including intermittent or continuous centrifugation. While a number of devices and systems are suitable, the preferred embodiment includes the use of commercially available devices and systems known to those of ordinary skill in the art. Exemplary devices and systems include, but are not limited to, those made by Haemonetics Corporation; Fenwal Laboratories; Cobe Laboratories; Asahi Medical Co., Ltd.; Baxter International, Inc., and Baxter Travenol Laboratories, Inc. Preferably, the separatory device 1 is an intermittent flow centrifugation (IFC) device, such as is conventionally used in the art. The biological fluid processing system according to the invention may include the component separation system and/or device.

Typically, the component separation system 90 provides for movement of the fluid by maintaining a pressure differential sufficient to cause the fluid to move from one location to another. For example, the component separation system may include, but is not limited to, at least one pump, such as a reversible or a non-reversible pump, to establish the pressure differential. In other embodiments, the pressure differential may be established by, for example, gravity head, using an expressor such as a mechanical, pneumatic or hydraulic expressor, by applying pressure by hand or with a pressure cuff, or by creating a vacuum.

While the component separation device and/or system may be manually controlled, the preferred embodiment is compatible with semi-automated or fully automated biological fluid processing operations. For example, using a microprocessor controlled device or system, once a source of a biological fluid such as a container or a donor is connected to the device and/or system, an appropriate sequence may be selected, and blood may be, automatically, withdrawn, the desired component(s) separated, and the component depleted biological fluid returned to the source. A representative example of such an automated system is a Haemonetics Model MCS Plus® apheresis system (Haemonetics Corporation, Braintree, Mass.).

In some embodiments, as will be noted in more detail below, at least one of leukocyte depletion of the separated component and separation of gas from the flow path of the separated component may also be under semi- or fully automated control.

GAS SEPARATION ARRANGEMENT

In accordance with the invention, the biological fluid processing system 10 may include a gas separation arrangement 100 to collect gas that may be present in the system and/or to separate gas from a biological fluid or from the flow path of the biological fluid. The gas separation arrangement 100 may separate gas from a biological fluid processing system. In some embodiments, the gas separation arrangement 100 may allow gas into the biological fluid processing system. As noted in more detail below, the gas separation arrangement may be used to minimize or prevent gas from reaching a filter assembly 6 such as a leukocyte depletion assembly and/or to minimize or prevent gas from reaching a downstream container 7 such as a receiving or collection container. The gas separation arrangement 100 may also be used for maximizing recovery of the biological fluid. In a sterile system, the gas separation arrangement 100 should provide for maintaining the sterility of the system.

The gas separation arrangement 100 includes at least one of a gas collection device and a gas separation device. Preferably, the gas separation arrangement 100 includes at least one gas collection device and at least one gas separation device.

In a preferred embodiment, the gas separation arrangement includes at least one porous element that allows gas to pass through the element, without the separated component passing through the element.

The placement of the gas separation arrangement 100 may be optimized to achieve a desired result. In a preferred embodiment, the gas separation arrangement 100 is located upstream of the filter assembly 6.

In accordance with the invention, the gas separation arrangement 100 may include a gas collection device 4 such as a drip chamber. The gas collection device 4 may be used to prevent gas from reaching a filter assembly 6 such as a leukocyte depletion assembly and/or to prevent gas from reaching a container 7 downstream of the gas collection device. The gas collection device 4 may be used to collect gas that is present in the system, and/or to separate gas from the flow path of a biological fluid. In some embodiments, the gas collection device may be used for maximizing recovery of the biological fluid.

The drip chambers which may be used in the biological fluid processing assembly may be constructed of any material compatible with biological fluid and gas. A wide variety of these drip chambers are already known in the art. The size of the drip chamber may be varied depending on, for example, the volume of fluid to be passed into the drip chamber and/or the number of cycles of processing.

The gas separation arrangement 100 may include at least one structure, device or element, preferably including a porous medium, that allows gas to be separated from a biological fluid being processed and/or to be separated from the flow path of the biological fluid being processed, e.g., allows gas out of a biological fluid processing system, but resists the passage of biological fluid. The gas separation arrangement 100 may also include at least one structure, device or element, that allows gas into a biological fluid processing system.

In a preferred embodiment, the gas separation arrangement 100 includes at least one gas separation device 3 such as a vent, more preferably a gas outlet, to improve the efficiency of gas separation from the biological fluid and/or from the flow path of the biological fluid. In some embodiments, at least one vent may be used to maximize the recovery of biological fluid in the downstream container. The gas separation device 3 should be chosen so that the sterility of the system is not compromised.

In a preferred embodiment, a vent such as a gas outlet allows gas that may be present in a biological fluid processing system out of the system. Thus, the gas outlet may provide for minimizing the volume of gases that remain in, or in contact with, a biological fluid during processing. In one embodiment, the gas outlet may also allow gas into the biological fluid processing system, and thus may function as a gas inlet.

The gas outlet comprises at least one porous medium, hereinafter referred to as a porous element, designed to allow gas to pass therethrough. A variety of materials may be used, provided the requisite properties of the porous element are achieved. These properties include the necessary strength to handle the differential pressures encountered in use and the ability to provide the desired permeability without the application of excessive pressure.

The gas outlet should be chosen so that the sterility of the system is not compromised. For example, the porous elements of the gas outlet should preferably have a bacterial blocking pore rating, e.g., of about 0.2 micrometer or less, to preclude bacteria entering the system.

Preferably, the gas outlet includes at least one liquophobic porous element. Because the liquophobic porous element is not wettable, or poorly wettable, by the biological fluid being processed in the system, gas in the system that contacts the liquophobic element will pass through it, and the biological fluid that is present will contact the element, but will not pass through.

The gas outlet may include at least one liquophilic porous element, that allows gas to exit, but, once the element is wetted with biological fluid, does not allow gas to enter, the system. Preferably the gas outlet includes both a liquophobic porous element and a liquophilic porous element. In a preferred embodiment of the invention, the outlet includes at least one liquophobic membrane and at least one liquophilic membrane, and the outlet allows gas to pass through the liquophilic membrane and then the liquophobic membrane until the liquophilic membrane is wetted by the biological fluid, at which time gas flow automatically stops, without biological fluid passing through the outlet.

Additionally, the gas outlet may include a housing, which may include a cap or closure. Exemplary gas outlets, and processes for using them are as disclosed in International Publication Nos. WO 91/17809 and WO 92/07656, and U.S. Pat. Nos. 5,126,054 and 5,217,627.

The components of the gas separation arrangement 100 and/or the configuration of the arrangement may be optimized to achieve a desired result. For example, in those embodiments including at least one gas collection device 4 such as a drip chamber, and at least one gas separation device 3 such as a gas outlet, the gas outlet its preferably located upstream of the drip chamber. In a preferred embodiment, the gas outlet is in communication with an anterior or upstream portion of the drip chamber. The gas outlet may be integrally connected to the drip chamber. Preferably, the gas outlet is located where gas is likely to be collected during processing, e.g., at or near the highest point of the drip chamber.

The gas separation arrangement 100 may include additional elements, such as, for example, at least one of a conduit, and a defoaming element.

FILTER ASSEMBLY

The biological fluid processing system 10 may include at least one filter assembly 6, i.e., a housing including an inlet and an outlet, and defining a flow path between the inlet and the outlet, with at least one porous medium interposed between the inlet and the outlet. In a more preferred embodiment, the filter assembly 6 comprises a leukocyte depletion device, and the porous medium comprises a leukocyte depletion medium.

A leukocyte depletion medium which may be used in accordance with the present invention comprises a porous medium suitable for depleting leukocytes from the fluid passing through the leukocyte depletion medium. Exemplary leukocyte depletion media include but are not limited to those disclosed in U.S. Pat. Nos. 5,217,627, 5,100,564 and 4,880,548 as well as International Publication Nos. WO 92/07656 and WO 91/04088. Additional exemplary leukocyte depletion media include those disclosed in U.S. Pat. Nos. 4,925,572, 4,923,620, and 5,229,012. These U.S. patents and International Publications also disclose exemplary housings for the leukocyte depletion media.

The containers which may be used in the biological fluid processing system may be constructed of any material and shape compatible with biological fluid and gas. A wide variety of these containers are already known in the art. For example, blood collection and satellite bags are typically made from plasticized PVC, e.g. PVC plasticized with dioctylphthalate, diethylhexylphthalate, or trioctyltrimellitate. The bags may also be formed from a polyolefin, polyurethane, polyester, or a polycarbonate.

As used herein, fluid communication may be established by any structure which allows the biological fluid and/or gas to pass from one location to another, such as by at least one conduit or tube. A flow control device such as a clamp, seal, valve, transfer leg closure, or the like, may be located within or on at least one of the conduits and/or the containers. The conduits used in the instant invention may be constructed of any material compatible with biological fluid and gas. Preferably, they may be composed of a flexible material, such as polyvinyl chloride (PVC), or plasticized PVC, e.g., PVC plasticized with dioctylphthalate, diethylhexylphthalate, or trioctyltrimellitate.

In accordance with the invention, the biological fluid processing system 10, which may be closed and/or sterile, may include additional elements or components, such as, but not limited to, at least one of a conduit, a connector, an injection port, and a container. The system may also include, for example, at least one vent such as a gas outlet, as described earlier, and/or at least one inlet.

For example, the biological fluid processing system may include a gas inlet to allow gas into the system. The gas inlet may allow gas into the system for maximizing recovery of the biological fluid. In a preferred embodiment, the gas inlet allows gas into the system so that separated component retained or entrapped in at least one element of the system can be recovered. In a sterile system, the gas inlet should provide for maintaining the sterility of the system. In one embodiment, the gas inlet comprises a porous element, more preferably, a porous element having a pore rating that blocks the entry of bacteria, e.g., a pore rating of about 0.2 micrometer or less.

Additionally, the gas inlet may include a housing, which may include a cap or closure. Exemplary gas inlets, and processes for using them are as disclosed in International Publication Nos. WO 91/17809 and WO 92/07656, and U.S. Pat. No. 5,217,627.

Preferably, the biological fluid processing system includes a sampling arrangement comprising at least one conduit and at least one additional container, such as a sampling container. In a more preferred embodiment, the sampling arrangement is in fluid communication with receiving container 7, and comprises a sampling container and at least one conduit, with the conduit providing fluid communication between the receiving container 7 and the sampling container.

In accordance with the invention, the biological fluid processing system 10 may include a gas collection and displacement loop 200 to collect gas, and optionally, to allow sampling of the separated component. In some embodiments, the collected gas may be used to recover additional biological fluid. In a preferred embodiment, the gas collection and displacement loop provides a safeguard that the separated component contaminated with leukocytes will be isolated from the leukocyte depleted separated component, since the contaminated fluid will not pass through at least one of the liquid barrier medium and the gas collection and displacement container, and into the receiving container 7.

The gas collection and displacement loop 200 includes at least one conduit, 250, 260, and/or 270, and at least one of a liquid barrier assembly 203 and a gas collection and displacement container 207. The liquid barrier assembly 203 comprises a housing including a porous liquid barrier medium that allows gas to pass through but bars the passage of liquid. Preferably, at least one flow control device, 230 and/or 240, is associated with at least one conduit of the gas collection and displacement loop.

In a preferred embodiment, as illustrated in FIG. 4, the gas collection and displacement loop 200 includes conduits 250, 260 and 270, liquid barrier assembly 203, and gas collection and displacement container 207. In the illustrated embodiment, the gas collection and displacement loop 200 is placed in fluid communication with the other components of the biological fluid processing system 10 via connectors 280 and 290. Preferred gas collection and displacement loops and methods for using them are disclosed in International Publication No. WO 93/25295.

In one embodiment, a method in accordance with the invention includes obtaining a biological fluid, typically including red cells, plasma, and platelets, from a source, separating at least one component, for example, platelets, from the biological fluid, returning the component depleted biological fluid to the source, and initiating further processing of the separated component, preferably before the return of the component depleted fluid to the source is completed. Further processing of the separated component includes at least one of separation of gas from the flow path of the component, preferably by passing the separated component through a gas separation arrangement, and leukocyte depletion of the component, preferably by passing the component through a leukocyte depletion device.

In accordance with the invention, the biological fluid may be processed, e.g., obtained from the source, the desired component separated, and the component depleted biological fluid returned to the source, two or more times. For example, in those embodiments wherein the source is a donor, the obtaining, separation and return as described above is preferably repeated at least twice during the apheresis period, i.e., the period between connecting the donor to the separation system 90, and disconnecting the donor.

The method may also include introducing gas into the separated component fluid flow path, e.g., to recover separated component trapped or entrained in at least one element of the biological fluid processing system.

Typically, the biological fluid is commingled with an additive fluid, for examples an anticoagulant, as is known in the art. Preferably, the biological fluid, e.g., whole blood, is commingled with an anticoagulant before the desired component is separated from the biological fluid. In a less desirable embodiment, the biological fluid may be mixed with an additive fluid and passed through a leukocyte depletion device before the desired component is separated from the biological fluid.

A variety of methods for withdrawing a biological fluid from a source, separating a desired component from the biological fluid, and returning the component depleted biological fluid to the source are known in the art. In the illustrated embodiment, a source of biological fluid, which may be a container of biological fluid, but is more preferably a donor such as a human or an animal, is connected to a separation system 90 which includes a component separatory device 1, so that at least one component of the biological fluid may be separated from the biological fluid. For example, a conventional apheresis system, more preferably a centrifugation system, even more preferably an intermittent flow centrifugation (IFC) system, may be connected to a donor and operated as is known in the art. In a more preferred embodiment, the method includes automatically withdrawing the biological fluid, separating the desired component from the biological fluid, and returning the component depleted biological fluid to the source.

Once separated from the biological fluid, the component is further processed, which includes separating gas from the flow path of the component and/or leukocyte depleting the component. For example, the separated component may be passed from the separation device 1 through at least one of a gas separation arrangement 100 and a filter assembly 6 such as a leukocyte depletion device. The processed component may then be collected in a container 7 such as a satellite bag or a receiving container. In some embodiments, the method includes automatically controlling the flow of the separated component to provide for at least one of separating gas from the flow path of the separated component and leukocyte depleting the separated component. For example, once the appropriate sequence is selected by the operator, a microprocessor may control the flow of the separated component by closing and opening flow control device 5.

Figure 2:
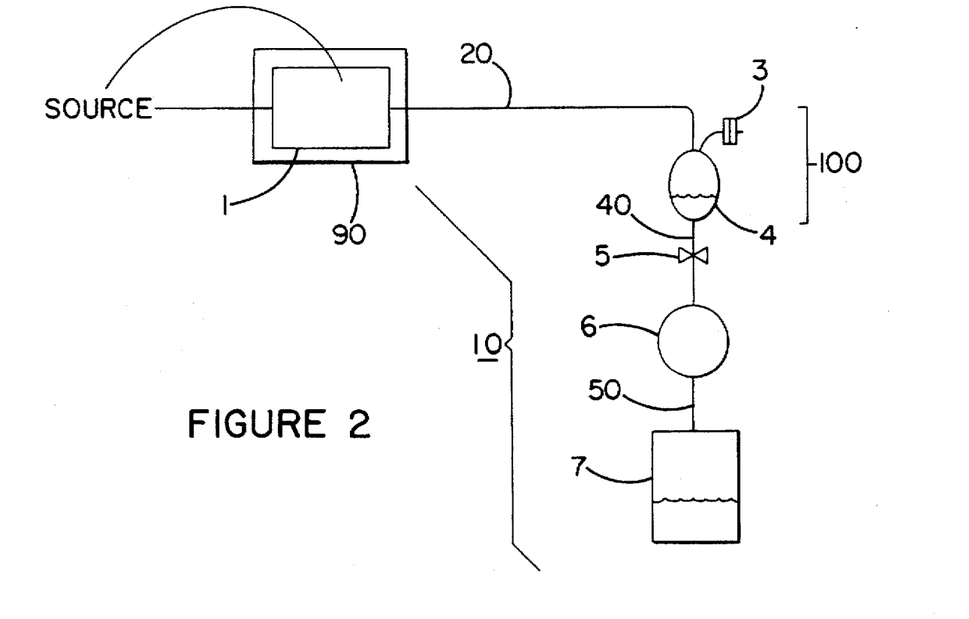
FIG. 2 is another embodiment of the present invention.
Figure 3:
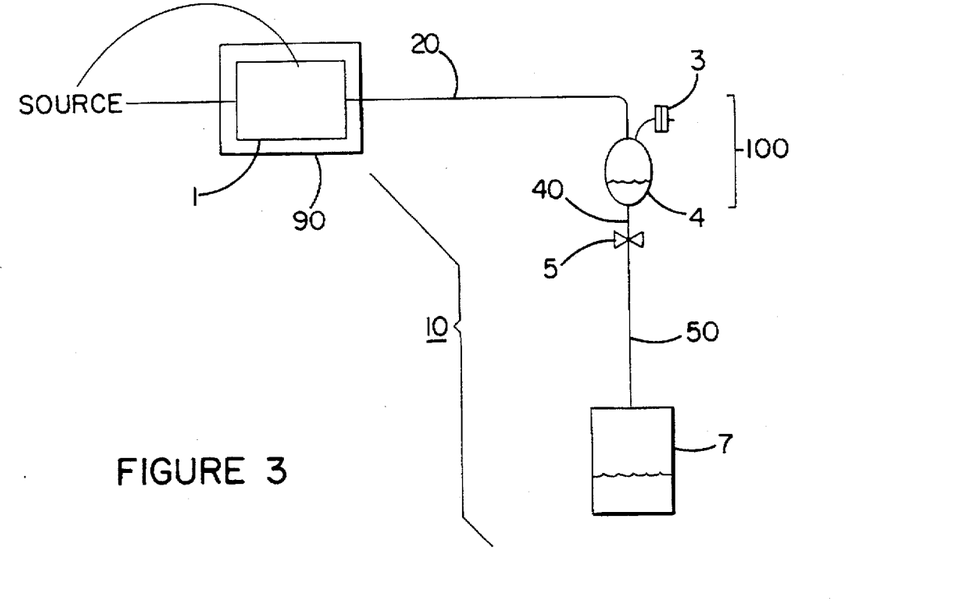
FIG. 3 is another embodiment of the present invention.

For convenience, the separated component will hereinafter be referred to as "the platelets", the "platelet containing fluid", or the "platelets suspended in plasma", but the invention is not to be so limited. The platelets may be passed from separation system 90 into biological fluid processing system 10 via conduit 20. The platelets may be passed directly to gas separation arrangement 100 as illustrated in FIGS. 2 and 3, or they may be passed directly to a filter assembly (not shown). Preferably, however, as shown in FIG. 1, the platelets are first passed to a container 2, such as a holding container, before passing them into the gas separation arrangement 100 and/or through a filter assembly 6 such as a leukocyte depletion device. In a less desirable embodiment, the platelet containing fluid may be passed though a filter assembly 6 before passing the fluid to container 2.

In some embodiments, e.g., including the use of a holding container, it may be desirable to decrease the presence of residual air or gas in the holding container before passing the platelets to the gas separation arrangement 100 and/or the filter assembly 6. In other embodiments, platelets may be passed to the holding container 2 and then to the gas separation arrangement 100 and/or the filter assembly 6 without depleting gas from the holding container. In an exemplary method for decreasing the presence of gas in the holding container, a vent such as a gas outlet may be interposed between the component separation system 90 and the holding container 2, or the vent may be located in or on holding container 2. In these embodiments, residual gas in the container 2 may be removed by passing at least a portion of the gas through the gas outlet before passing platelets into the container 2 and then toward the gas separation arrangement 100. For example, the vent may be opened and the holding container 2 may be compressed, preferably while flow control device 5 is closed, to pass gas through the gas outlet to minimize the presence of air before closing or clamping the vent and then passing the platelets into the container 2. Preferably, gas is passed through the vent while maintaining the sterility of the system.

With respect to FIG. 1, at least one flow control device 5 such as a clamp may be used to control the flow of the platelets. Preferably, flow control device 5 is initially closed, and the platelets suspended in plasma are passed from the holding container 2 toward the gas separation arrangement 100, which drives gas ahead of the separated component into the gas separation arrangement 100, where gas is separated from the platelet flow path, e.g., gas is collected in the gas separation arrangement 100. In a preferred embodiment, gas is collected in gas collection device 4 and passed through gas separation device 3.

In those embodiments wherein gas collection device 4 is a drip chamber, gas driven ahead of the platelets is collected in the drip chamber and/or gas bubbles are coalesced in the drip chamber. In a more preferred embodiment, wherein gas collection device 4 is a drip chamber and gas separation device 3 is a gas outlet, the method includes filling the drip chamber with gas displaced by the platelets. Collected gas rises to the upper portion of the drip chamber. The gas outlet may be activated, e.g., uncapped, or a clamp between the gas outlet and the drip chamber is opened, and gas then passes through the gas outlet, and platelets pass into the drip chamber. In a more preferred embodiment, the gas outlet lacks a cap, and there is no clamp between the outlet and the drip chamber, so that gas passes through the gas outlet and the drip chamber fills with platelets without uncapping or unclamping.

While the passage of gas through the gas separation device 3 may be manually stopped, e.g., by capping or clamping, in a preferred embodiment, the gas separation device 3 comprises a gas outlet which includes a porous element that allows gas to pass therethrough until the element is wetted by the platelet containing fluid, and gas flow stops automatically, without capping or clamping.

Once the flow of gas through the gas outlet is terminated, flow control device 5 may be opened, manually or automatically, and platelet containing fluid will pass from gas separation arrangement 100 through conduit 40 into the downstream container or receiving bag 7. In a preferred embodiment, as illustrated in FIG. 1 and 2, a filter assembly 6 such as a leukocyte depletion device is interposed between the gas separation arrangement 100 and the container or receiving bag 7. Once flow control device 5 is opened, platelets pass through a leukocyte depletion device and the leucocyte depleted platelets then pass into the downstream container or receiving bag 7.

Preferably, the method comprises an apheresis period including more than one complete biological fluid processing cycle of withdrawal of biological fluid, and component separation followed by the return of the component depleted biological fluid to the source. For example, the apheresis period in accordance with the invention typically includes about six to about eight complete cycles. These cycles may be automatically controlled.

Typically, the separation of gas from the flow path of the platelets, and/or the leukocyte depletion of the platelets, begins or is initiated during each cycle, e.g., while the platelets are being separated from the biological fluid, or, more preferably, while the remaining platelet depleted biological fluid, e.g., red blood cell containing fluid, is being returned toward the source of the fluid, e.g., the donor. In some embodiments, the separation of gas from the platelets, and/or the leukocyte depletion of the platelets, is completed or essentially completed during each cycle, e.g., while the platelet depleted biological fluid is returned to the source of the fluid.

In yet another embodiment, the separation of gas from the platelet flow path, and/or the leukocyte depletion of the platelets, is initiated during different cycles within the apheresis period. For example, platelets may be accumulated, e.g., in a container such as a holding container, during two or more cycles, and platelet depleted biological fluid may be returned to the source during each of these cycles. However, further processing of the accumulated platelets may be initiated later in the apheresis period, i.e., before a later cycle of return of the platelet depleted biological fluid to the source is completed. The method may include repeatedly accumulating the separated component during a plurality of cycles and further processing the accumulated component during a later cycle in the apheresis period.

Typically, in those embodiments including more than one cycle and the use of a gas separation arrangement 100, more gas may be separated in the gas separation arrangement during the first cycle than in subsequent cycles. For example, since the holding container 2, and/or the conduits 20, 30 may include air, the passage of platelets in the system during the first cycle may displace this air into the gas separation arrangement 100, where it may be separated from the platelet fluid flow path, e.g., to prevent gas from passing into the filter assembly 6. During subsequent cycles, since air has already been displaced from various elements of the system, less additional air may have to be separated from the platelet flow path.

Generally, in those embodiments including more than one cycle and the use of a gas separation arrangement 100 including a drip chamber and a gas outlet that automatically stops the flow of gas once the porous element of the gas outlet is wetted, the gas outlet is utilized and the drip chamber is filled during the first cycle, e.g., until the element in the outlet is wetted with biological fluid. In this embodiment, while the drip chamber is preferably utilized during subsequent cycles, i.e., including passing the separated platelets to a receiving container, the gas outlet is preferably not utilized during these cycles. Accordingly, the drip chamber provides for gas collection and gas separation during these subsequent cycles.

In a more preferred aspect of this embodiment of the invention, as illustrated in FIG. 1, the gas separation arrangement 100 is located downstream of holding container 2, and the gas separation arrangement may be utilized during the first cycle as noted above. Thus, after flow control device 5 is closed, platelets are passed from container 2 (which is preferably a flexible container), through conduit 30, into gas separation arrangement 100. The drip chamber fills, gas passes through the gas outlet until the porous element in the outlet is wetted and gas flow through the outlet stops. Flow control device 5 is then opened, and platelets pass into conduit 40 and through filter assembly 6 into container 7. Preferably, in those embodiments wherein holding container 2 is a flexible container, once container 2 has drained, the inner walls of the container contact one another, e.g., near the connection to conduit 30, sealing the fluid flow path between the container 2 and the conduit 30, thus stopping the flow of platelets without closing flow control device 5.

During subsequent cycles, which allow additional platelets to flow into and out of container 2, flow control device 5 may remain open, since the flow of platelets may automatically be terminated once the inner walls of container 2 contact each other. Generally since less air should be present during subsequent cycles, little air will pass from the container 2 into conduit 30 during subsequent cycles. Accordingly, the drip chamber provides for separation of gas from the platelet flow path during these subsequent cycles, so that little or no air will enter the filter assembly 6.

In other embodiments, including a drip chamber and a gas outlet that does not stop the flow of gas once the porous element is wetted, the gas outlet and the drip chamber may be utilized during these additional cycles. Accordingly, the gas outlet may be activated, e.g., uncapped/unclamped, or inactivated, e.g., capped/clamped, as is desirable during the method. For example, the gas outlet is activated whenever it is desirable to pass gas through the outlet, and the outlet is inactivated otherwise. Preferably, in those embodiments including the use of a holding container, the gas outlet may be utilized during the first cycle, and the drip chamber may be utilized during all of the cycles, as described previously.

Thus, in those embodiments including a plurality of cycles, as additional platelet containing fluid is separated from the biological fluid and passed to the receiving container 7, gas maybe separated from the platelet flow path during passage through the drip chamber 4. The size of the drip chamber may be varied depending on the volume of platelet containing fluid to be processed and/or the number of cycles of processing.

The platelet containing fluid passes through a separate and isolated flow path than the unseparated biological fluid and the platelet depleted biological fluid. Movement of the platelet containing fluid through the system may be effected by maintaining a pressure differential between elements of the system, e.g., wherein one element contains the platelet fluid and another element is the intended destination of the fluid. For example, a pressure differential may be created between receiving container 7 and either one end of conduit 20 (e.g., at separation device 1 in an embodiment without holding container 2), or holding container 2, so as to cause the fluid to flow in a desired direction, i.e., toward the receiving container. The pressure differential may be automatically controlled, or it may be manually controlled.

Preferably, the pressure differential allows the platelet containing fluid to pass from one location to another at a rate independent of the flow rate of the unseparated biological fluid (e.g., as the unseparated biological fluid passes from the source to the component separation device 1) and/or the flow rate of the platelet depleted biological fluid (e.g., as it passes from the component separation device 1 toward the source).

For example, fluid may be passed from the source to the separation device and/or passed from the separation device to the source at a flow rate of greater than about 35 ml/minute, e.g., about 50 to about 80 ml/minute during plateletpheresis, or about 50 to about 150 ml/minute during separation of red cells. However, in accordance with the invention, once the platelet containing fluid has been separated from the biological fluid, a pressure differential may be created, e.g., a gravity head between the holding container 2 and the receiving container 7, and the platelet containing fluid may be passed through the filter assembly 6 at a flow rate of less than about 25 ml/minute. In those embodiments wherein the filter assembly is a leukocyte depletion assembly, this slower rate provides for more efficient leukocyte depletion, since, for example, more of the platelet containing fluid may contact the leukocyte depletion medium. In a more preferred embodiment, the platelets may be passed through the leukocyte depletion device at a flow rate in the range of, for example, about 10 to about 20 ml/minute.

Exemplary methods for creating a pressure differential to allow platelets to flow through the leukocyte depletion device at this independent rate include, but are not limited to, using gravity head, a pump, an expressor such as a mechanical, pneumatic or hydraulic expressor, applying pressure by hand or with a pressure cuff, or creating a vacuum. For example, with respect to the Figures, the biological fluid processing system 10 may be arranged such that receiving container 7 is placed at the lowest point, and the gravity head will cause the platelets to flow toward the container 7. In a more preferred embodiment, as illustrated in FIGS. 1 and 4, holding container 2 may be placed above receiving container 7, so that platelets will flow from the holding container 2, through the gas separation arrangement 100 and the filter assembly 6, into receiving container 7.

In some embodiments, particularly those including passing the platelets through a filter assembly such as a leukocyte depletion device and into a downstream container, the method includes recovering the valuable platelets that may remain entrapped in the system once the pressures differential is sufficiently decreased. For example, once holding container 2 (e.g., in FIGS. 1 and 4) and/or conduit 20 (e.g., in FIGS. 1, 2 and 4) have sufficiently drained, platelet flow may stop, leaving platelets in the leukocyte depletion device and/or the conduit upstream of the leukocyte depletion device. In accordance with the invention, gas may be added to the platelet fluid flow path to recover additional platelet containing fluid.

For example, in a more preferred embodiment, after the final separation cycle, gas may be added to a section of the separated platelet containing fluid flow path, so that additional platelets, e.g., in the holding container and/or the leukocyte depletion device, may be passed into the receiving container. Preferably, the recovery of this additional liquid may be essentially completed contemporaneously with the disconnection of the system from the donor. For example, the donor may be disconnected from the separation system as gas is being added to the platelet fluid flow path, e.g., at conduit 20, and the flow of this additional platelet containing fluid into the receiving container may be completed shortly thereafter, e.g., about 15 seconds, after the donor is disconnected from the separation system.

With reference to FIGS. 1 and 4, gas may be introduced into the fluid flow path at any desired location, e.g., upstream of holding container 2; upstream of gas separation arrangement 100; within gas separation arrangement 100, e.g., in the drip chamber or through the gas outlet; or between the drip chamber and filter assembly 6. Preferably, air is introduced without compromising the sterility of the system. Exemplary devices and techniques for the introduction of air include, but are not limited to, utilizing gas inlets as disclosed in International Publication No. WO 91/17809, and/or utilizing gas collection and displacement loops as disclosed in International Publication No. WO 93/25295.

For example, a gas inlet as disclosed in International Publication No. WO 91/17809, or one end of a gas collection and displacement loop as disclosed in International Publication No. WO 93/25295, may be associated with conduit 20, conduit 30, holding container 2, or gas collection device 4. Before introducing air, but after the final separation cycle, platelets suspended in plasma may be passed from the holding container 2, through the gas separation arrangement 100 and the filter assembly 6, and into receiving container 7, until flow into the receiving container stops.

In those embodiments including a gas inlet, the inlet, which may be automatically or manually controlled, may be opened or activated, and additional platelet containing fluid trapped or retained in the system, e.g., in conduit 20, 30 and/or 40, holding container 2, the drip chamber, and/or in the upstream portion of filter assembly 6, may drained into the receiving container 7 and recovered.

In those embodiments including a gas collection and displacement loop 200, e.g., as illustrated in FIG. 4, gas may be passed through the gas collection and displacement loop and into the platelet fluid flow path, e.g., upstream of the filter assembly 6. For example, since the passage of platelets into receiving container 7 during the first cycle may displace gas (e.g, in conduit 50) into the receiving container, this gas may be passed from the container 7 into the gas collection and displacement loop 200. Illustratively, receiving container 7 may be compressed to pass gas, and, optionally, platelets for sampling, through connector 280 and conduit 250 into gas collection container 207. Gas may then be passed from gas collection container 207, through conduit 260, through liquid barrier assembly 203, conduit 270 and connector 290, and toward filter assembly 6, thus allowing additional platelets to drain into receiving container 7.

Illustratively, with respect to FIG. 4, passing gas through the gas collection and displacement loop 200 and through connector 290 may allow the drainage of platelets from conduits 30 and 40, as well as from gas collection device 4 and the upstream of filter assembly 6, into container 7. In other embodiments, one end of conduit 270 of the gas collection and displacement loop 200 may be associated with, for example, conduit 20 or holding container 2, and the passage of gas into these elements may allow additional platelets to be recovered.

In a preferred embodiment, the platelets may be recovered in container 7 and utilized at the appropriate time, e.g, after storage. In some embodiments, for example, in those embodiments including a sampling arrangement instead of a gas collection and displacement loop, a portion of the platelets may be passed from container 7 to an additional container, the sampling container, so that this sample in the additional container may be tested before utilizing the platelets in receiving container 7. For example, the system may include a sampling arrangement comprising a sampling container and at least one conduit providing fluid communication between the sampling container and the receiving container 7, so that gas and platelets may be passed from the receiving container 7 through the conduit and into the sampling container, and the platelets may be sampled at the appropriate time.

With respect to utilizing the gas collection and displacement loop for sampling, since gas and platelets may be passed from container 7 into gas collection container 207 of gas collection and displacement loop 200 as described above, the gas may then be passed from gas collection container 207 through liquid barrier assembly 203 into conduit 270 of the loop 200, while leaving platelets for sampling in container 207. The gas passed from the gas collection container 207 may be used to recover additional platelets as noted above, and the platelets may be sampled at the appropriate time. In a preferred embodiment, after a desired amount of platelets for sampling have been passed into gas collection container 207, and the displaced gas has been passed through the loop 200 so that additional platelets have been recovered in container 7, containers 7 and 207, along with conduit 250, are removed from the system, and stored until the platelets in container 7 are to be used.

For example, once a sample of platelets has been passed into collection container 207 and the additional platelets are recovered in container 7, conduit 50 is heat sealed between connector 280 and filter assembly 6, and conduits 250 and 260 are heat sealed, thus allowing the removal, as a unit, of containers 7 and 207 along with conduit 250 interposed between the containers.

Further embodiments are encompassed by the present invention. For example, in one embodiment, after the desired component, e.g., platelets, is separated from the biological fluid, the platelet depleted biological fluid may be passed through a leukocyte depletion device before it is returned to the source. For example, whole blood may be obtained from a donor, and platelets may be separated from the blood. The platelet depleted blood may be passed through a leukocyte depletion device, and the blood, depleted of platelets and leukocytes, may be returned to the donor. In another embodiment, a biological fluid may be obtained from a source and passed through a leukocyte depletion device before the platelets are separated from the biological fluid. In these embodiments, the separated platelets may be further processed as noted above, i.e., passed through the gas separation arrangement 100 and/or the filter assembly 6.

As noted earlier, the separated component is not limited to platelets. Accordingly, in other illustrative embodiments, the separated component may be, for example, red cells, and the method may include returning red cell depleted blood to the source, and, during the apheresis period, at least one of passing red cells to a gas separation arrangement to separate gas from the flow path of the red cells and leukocyte depleting the red cells by passing them through a leukocyte depletion medium.

EXAMPLES

Example 1

The biological fluid processing system used to perform this example includes a 100 ml plastic container, a 600 ml plastic container, a drip chamber, and a gas outlet, set up in manner that generally corresponds to that described for FIG. 1. The system is arranged generally vertically, and the 100 ml container, the holding container, is hung at a distance of about 12 inches above the 600 ml container, the receiving container.

The leukocyte depletion assembly, which is produced in accordance with U.S. Pat. No. 4,880,548, is hung at a distance of approximately 4 inches from the holding container. The gas outlet, which is produced in accordance with International Publication No. WO 91/17809, and includes a porous element that blocks bacteria, and stops the passage of gas once wetted with biological fluid, is integrally connected to the drip chamber, which is a commercially available 20 ml drip chamber.

The biological fluid processing system is connected to a Haemonetics Model MCS Plus® apheresis system (Haemonetics Corporation, Braintree, Mass.). Since this apheresis system includes a conduit for passing the separated component, this conduit is connected to the biological fluid processing system via sterile docking.

A manually operable clamp is located on the conduit between the drip chamber and the leukocyte depletion assembly. The clamp is initially closed.

A donor is connected to the Haemonetics Model MCS Plus® apheresis system and the system is operated according to the manufacturer's instructions. Blood is withdrawn from the donor, mixed with anticoagulant, and passed to the centrifuge at a flow rate of about 60 ml/minute to separate platelets from the blood. The separated platelets are passed to the holding container.

As platelet-depleted blood is returned to the donor along one flow path, the separated platelets pass along a separate flow path from the holding container toward the drip chamber, and gas is displaced into the drip chamber. The drip chamber fills with gas, gas passes through the porous element of the gas outlet, and platelets enter the chamber. The chamber fills with platelets, which eventually contact the porous element of the gas outlet, and gas flow stops, without platelets passing through the porous element.

The clamp between the drip chamber and the leukocyte depletion assembly is opened. Platelets prime the leukocyte depletion assembly, and pass through the assembly at a flow rate of about 20 ml/minute, and into the downstream receiving container. Once the holding container is sufficiently emptied, the inner walls of the container contact each other, and platelet flow stops.

Another cycle of withdrawal of blood from the donor is initiated, and platelets are separated and passed to the holding container as noted above. Once sufficient platelets enter the holding container, the inner walls of the container are spread apart, and platelets flow through the drip chamber and the leukocyte depletion assembly, and into the receiving container. While platelet depleted blood is returned to the donor, the platelets drain out of the holding container. Once the holding container is sufficiently drained, the inner walls contact each other, and flow steps as described previously.

This withdrawal of blood, separation, return, and passage of platelets into the receiving container is repeated four more times, to obtain the desired amount of platelets. The platelets are found to be highly depleted of leukocytes, i.e., less than about $5 \times 10^5$/unit.

Example 2

This Example is set up and performed generally in accordance with that described in Example 1. However, in this Example, the biological fluid processing assembly includes a leukocyte depletion assembly produced in accordance with U.S. Pat. No. 4,925,572, and the 100 ml holding container is hung at a distance of about 20 inches above the 600 ml receiving container. The leukocyte depletion assembly is hung at a distance of approximately 4 inches from the holding container.

Additionally, the Haemonetics Model MCS Plus® apheresis system in this Example is operated to separate red cells from the blood, rather than to separate platelets from the blood as described in Example 1.

The withdrawal of blood, separation, return, and passage of the separated component through the gas separation arrangement and then the leukocyte depletion assembly into the receiving container is generally performed as described in Example 1, to obtain the desired amount of red cells. However, the receiving container is hung about 20 inches below the holding container in this Example, rather than about 12 inches below, as in Example 1. The red cells pass through the leukocyte depletion assembly at a rate of about 20 ml/minute. The red cells are found to be highly depleted of leukocytes, i.e., less than about $5 \times 10^5$/unit.

Example 3

The Example is set up and performed generally in accordance with that described in Example 1. However, the biological fluid processing system in this Example also includes a sampling arrangement comprising a conduit and a 50 ml plastic container, the sampling container. A Y-connector, downstream of the leukocyte depletion assembly, is interposed between the assembly and the receiving container. One end of the conduit of the sampling arrangement is connected to the Y-connector, and the other end of the conduit is connected to the 50 ml sampling container. The sampling arrangement also includes an injection port in fluid communication with the sampling container. All of the connections are via sterile docking.

The platelets are passed into the receiving container as described in Example 1. The receiving container is compressed, passing gas and about 20 ml of platelets through the Y-connector and into the sampling container. The conduits between the leukocyte depletion assembly and the receiving container, and between the Y-connector and the sampling container are heat sealed, and the receiving container and the sampling arrangement are separated as a unit from the rest of the biological fluid processing system.

Platelets are withdrawn for sampling with the injection port in fluid communication with the sampling container.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for intermittent flow centrifugation plateletpheresis comprising;
   withdrawing blood from a donor using a pressure differential to pass the blood in a first direction;
   separating platelet containing fluid from the blood by centrifugation;
   returning the platelet depleted blood to the donor using a pressure differential to pass the platelet depleted blood in a reverse direction while, utilizing a separate flow path;
   separating gas from the flow path of the platelet containing fluid by passing the platelet containing fluid through a gas separation arrangement, and then,
   passing the platelet containing fluid through a leukocyte depletion medium.

2. The method of claim 1 further comprising collecting the platelet containing leukocyte depleted fluid in a receiving container.

3. The method of claim 1, wherein withdrawing the blood from a donor occurs at a rate greater than 35 ml/min.

4. The method of claim 1, wherein returning the platelet depleted blood in a reverse direction occurs at a rate greater than 35 ml/min.

5. The method of claim 1, further comprising accumulating the platelet containing fluid prior to passing the platelet containing fluid through a leukocyte depletion medium.

6. The method of claim 1, further comprising accumulating the platelet containing fluid prior to separating gas from the flow path of the platelet containing fluid.

7. A method for processing a biological fluid comprising:
   obtaining a biological fluid comprising red blood cells and platelets from a source;
   separating platelets from the biological fluid to deplete the biological fluid of platelets;
   returning platelet-depleted red blood cell-containing biological fluid to the source while:
   separating gas from a flow path of the separated platelets; and,
   passing a portion of the separated platelets along the flow path and through a leukocyte depletion medium to deplete leukocytes from the separated platelets.

8. The method of claim 7 wherein the source is a donor, the method including withdrawing biological fluid from the donor, and
   depleting leukocytes from the separated platelets and returning platelet-depleted red blood cell-containing biological fluid to the donor.

9. The method of claim 8 wherein withdrawing the biological fluid from the donor, separating platelets from the biological fluid, and returning platelet-depleted red blood cell-containing biological fluid to the donor includes intermittent flow centrifugation.

10. The method of claim 8 wherein withdrawing the biological fluid from the donor, separating platelets from the biological fluid, and returning platelet-depleted red blood cell-containing biological fluid to the donor includes continuous flow centrifugation.

11. The method of claim 7 further comprising separating gas from the flow path of the separated platelets before leukocyte depleting the separated platelets.

12. The method of claim 11 wherein separating gas from the flow path of the separated platelets includes passing the separated platelets into a gas separation arrangement.

13. The method of claim 12 wherein passing the separated platelets into a gas separation arrangement includes passing gas through a gas outlet and passing the separated platelets through a drip chamber.

14. The method of claim 13 wherein passing gas through a gas outlet includes passing gas through a porous medium until platelet containing fluid contacts the porous medium and gas flow stops automatically.

15. The method of claim 13 further comprising passing the leukocyte depleted platelets into a container.

16. The method of claim 7, further comprising accumulating the separated platelets prior to passing a portion of the separated platelets through a leukocyte depletion medium.

17. The method of claim 7, further comprising adding gas to the flow path of the separated platelets after passing a portion of the separated platelets through a leukocyte depletion medium.

18. A method for processing a biological fluid comprising:
   withdrawing a biological fluid comprising red blood cells and platelets from a donor;

separating platelets from the biological fluid to deplete the biological fluid of platelets;

returning platelet-depleted red blood cell-containing biological fluid to the donor while:

separating gas from a flow path of the separated platelets; and, passing the separated platelets along the flow path and through a leukocyte depletion medium to deplete leukocytes from the separated platelets.

19. The method of claim 18 further comprising separating gas from the flow path of the separated platelets before leukocyte depleting the platelets; and wherein separating gas from the flow path of the separated platelets includes passing the separated platelets into a gas separation arrangement.

20. The method of claim 19 wherein passing the separated platelets into a gas separation arrangement includes passing gas through a gas outlet and passing the separated platelets through a drip chamber.

21. The method of claim 20 wherein passing gas through a gas outlet includes passing gas through a porous medium until platelet containing fluid contacts the porous medium and gas flow stops automatically.

22. The method of claim 18, wherein withdrawing a biological fluid occurs at a rate of greater than 35 ml/min.

23. The method of claim 18, wherein returning the platelet-depleted red blood cell-containing biological fluid to the donor occurs at a rate greater than 35 ml/min.

24. The method of claim 18, further comprising accumulating the separated platelets prior to separating gas from the flow path of the separated platelets.

* * * * *